United States Patent [19]

Kortenbach et al.

[11] Patent Number: 5,313,935
[45] Date of Patent: May 24, 1994

[54] APPARATUS FOR COUNTING THE NUMBER OF TIMES A SURGICAL INSTRUMENT HAS BEEN USED

[75] Inventors: Jurgen A. Kortenbach, Miami Springs; George Nunez, Miami; Charles R. Slater, Fort Lauderdale, all of Fla.

[73] Assignee: Symbiosis Corporation, Miami, Fla.

[21] Appl. No.: 107,456

[22] Filed: Aug. 17, 1993

Related U.S. Application Data

[63] Continuation-in-part of Ser. No. 16,596, Feb. 11, 1993, and a continuation-in-part of Ser. No. 998,951, Dec. 31, 1992, and a continuation-in-part of Ser. No. 999,228, Dec. 31, 1992.

[51] Int. Cl.⁵ .............................................. A61B 1/00
[52] U.S. Cl. ........................................ 128/4; 606/205; 116/221; 116/284
[58] Field of Search ............... 116/206, 207, 216, 221, 116/284; 235/131 JA, 139 A, 142, 144 ME; 128/4; 606/205

[56] References Cited

U.S. PATENT DOCUMENTS 5,143,453 9/1992 Weynant nee Girones ... 116/221 X

Primary Examiner—Richard J. Apley
Assistant Examiner—Beverly A. Meindl
Attorney, Agent, or Firm—David P. Gordon

[57] ABSTRACT

An improved use counter for endoscopic instruments is mounted in the ferrule of the distal portion of an endoscopic instrument having separable proximal and distal portions. The counter includes a ratchet wheel having inner and outer teeth and a bimetallic coil having a fixed end and a free end. The fixed end of the bimetallic coil is attached to a hub portion of the ferrule and the free end of the bimetallic coil engages the inner teeth of the ratchet wheel. An inwardly extending tooth in the ferrule engages the outer teeth of the ratchet wheel to prevent backward movement of the ratchet wheel. The outer surface of the ratchet wheel is also provided with incremental indicia viewable through a window in the ferrule. As the bimetallic coil is heated and cooled when the instrument is sterilized, the free end of the coil engages and advances one tooth of the ratchet wheel. Movement of the free end is preferably limited by stops. A spring biased locking and disabling pin is mounted in the ferrule and engages a stepped width portion of the ratchet wheel. The pin prevents advancement of the ratchet wheel during shipping and disables the instrument after a predetermined number of sterilizations.

19 Claims, 6 Drawing Sheets

APPARATUS FOR COUNTING THE NUMBER OF TIMES A SURGICAL INSTRUMENT HAS BEEN USED

This application is a continuation-in-part of application Ser. No. 08/016,596, filed Feb. 11, 1993, Ser. No. 07/998,951, filed Dec. 31, 1992, and Ser. No. 07/999,228, filed Dec. 31, 1992, which are hereby incorporated by reference herein in their entireties.

BACKGROUND OF THE INVENTION

This invention relates to surgical instruments. More particularly, this invention relates to an apparatus for automatically counting the number of times a surgical instrument has been sterilized. This invention finds particular use in endoscopic surgical instruments which are preferably disposed of after a certain number of uses.

Endoscopic surgery is widely practiced throughout the world today and its acceptance is growing rapidly. In general, endoscopic surgery involves one or more incisions made by trocars where trocar tubes are left in place so that endoscopic surgical instruments may be inserted through the tubes. A camera, lens, or other optical instrument is often inserted through a first trocar tube, while a cutter, dissector, or other surgical instrument is inserted through a second trocar tube for purposes of manipulating and/or cutting the internal organ. It is often desirable to have several trocar tubes in place at once in order to receive several surgical instruments. In this manner, an organ or tissue may be grasped with one surgical instrument, and simultaneously may be cut with another surgical instrument; all under view of the surgeon via the optical instrument in place in a trocar tube.

By 1996, it is expected that more than two million additional endosurgeries will be performed per year that, in 1990, were done via open surgery (MedPRO Month, I:12, p. 178). The advantages of endoscopic surgery are clear in that it is less invasive, less traumatic and recovery is typically quicker. As a result, many new instruments and devices for use in endosurgery are introduced every year. Most endoscopic instruments have similar configurations with a proximal handle, an actuation mechanism, and distal end effectors coupled by a tube through which the actuation mechanism extends. The end effectors take many forms such as grippers, cutters, forceps, dissectors and the like. Some endoscopic instruments are provided with a ferrule on the tube so that the tube which carries the end effectors can be rotated relative to the handle. Initially, endoscopic surgical instruments were very expensive, partly because they must be very small but still durable and reliable and the materials necessary to provide these features are expensive.

Recently, a number of "disposable" endoscopic instruments have been introduced and their use is now widely accepted. One of the advantages of disposable endoscopic instruments over reusable instruments is that because they are used only a single time, there are no sterilization problems, and no concerns about the dulling or nicking of blades or wearing of parts. However, in order to justify disposing of instruments after a single use, the instruments have to be much less expensive than the reusable tools. In order to manufacture the instruments less expensively, the disposable instruments therefore use less expensive materials. As a result, the disposable instruments are less durable than the reusable instruments, which is not of concern where the instruments are used only once. However, in order to reduce the costs of medical procedures, many hospitals and surgeons have recently started to sterilize and reuse the "disposable" endoscopic instruments. This practice can be problematic. While the disposable endoscopic instruments typically are not so fragile that they must be disposed of after a single use, clearly, they may not be used as many times as the typical stainless steel reusable instruments as they are more likely to malfunction and dull after several uses. Presently, there is no scientific mechanism available for determining how many times a medical instrument has been used, and the surgeon or the surgical staff must devise their own system to keep track of the number of times a tool has been used so that it will not be used after its useful life has expired.

Parent application Ser. No. 07/998,951 discloses an apparatus for counting the number of times a surgical device has been sterilized. The apparatus includes an indicator having sequential indicia and a heat responsive member for indicating a next one of the indicia. Mechanical, fluid mechanical and electronic versions of the invention are disclosed. In one of the mechanical versions, the indicator is a ratchet member having teeth, a direction limiting pawl, and a display surface containing indicia. A heat responsive element such as a bimetallic member engages the teeth of the ratchet and advances the ratchet each time the apparatus is subjected to the heat of sterilization. The direction limiting pawl prevents the ratchet member from moving backwards once it is advanced. A housing with a window can mask the display to indicate one of the indicia as advanced by the heat responsive element. Preferred embodiments of the mechanical version disclosed in the parent application thereto include a ring-like ratchet member with interior teeth and an exterior display surface. The number of teeth is preferably one or more less than the number of indicia so that upon advancing the ratchet member to the last indicia, it can be advanced no further. The bimetallic element is mounted inside the ring and the housing covers the outer surface of the ring. The housing may be formed from the ferrule of an endoscopic surgical tool or may be formed as part of the handle of such a tool. A disengagable locking pin is provided to prevent movement of the ratchet member during shipping and the locking pin may be coupled to packaging so that it is automatically removed when the surgical tool is removed from its packaging.

Parent application Ser. No. 07/999,228 discloses an apparatus for counting the number of times a temperature cycle occurs which includes an indicator having sequential indicia and a temperature responsive member for indicating a next one of the indicia. Again, mechanical, fluid mechanical and electronic versions of the invention are disclosed, and in the mechanical version, the indicator can be a ratchet member having teeth, a direction limiting pawl, and a display surface containing indicia. A temperature responsive element such as a bimetallic member engages the teeth of the ratchet and advances the ratchet each time the apparatus is subjected to a preset temperature cycle. A housing with a window masks the display to indicate one of the indicia as advanced by the temperature responsive element. Preferred embodiments of this mechanical version include a ring-like ratchet. member with interior teeth and an exterior display surface The number of teeth is preferably one or more less than the number of indicia so that upon advancing the ratchet member to the last indicia, it can be advanced no further. The bimetallic element is mounted inside the ring and the housing covers the outer surface of the ring. A disengagable locking pin is provided to prevent movement of the ratchet member until activated.

The mechanical embodiments of the parent applications have a few disadvantages when miniaturized for use, for example, with endoscopic surgical instruments. First, the direction limiting pawl which is used to prevent backward movement of the ratchet member must be very small, e.g., approximately 0.15 inches long with a diameter of approximately 0.01 inches. Moreover, in an exemplary embodiment used with endoscopic surgical instruments, the depth of ratchet teeth is only approximately 0.015 inches. Given the relative criticality of alignment necessary to permit accurate functioning of the counter, these dimensions make the direction limiting pawl difficult and/or expensive to manufacture in large amounts. While, an escapement mechanism was suggested as an alternative to the direction limiting pawl when used with a rotating ratchet member, because the escapement mechanism would be driven by the free end of the bimetallic member, realization of this embodiment would also be difficult and/or expensive in large amounts.

Another minor disadvantage of the mechanical embodiments of the parent applications involved the use of disengagable locking pins which was used to prevent activation of the counter. It was recognized, however, that by leaving the pin engaged in the counter during sterilization, the counter mechanism could be defeated.

Patent application Ser. No. 08/016,596 discloses endoscopic instruments having a reusable portion (the handle and actuating means) and a disposable portion (the tube, push rod and end effectors). The two portions can be coupled and uncoupled so that the disposable portion may be disposed of while the reusable portion may be reused with a new disposable portion. As with the completely disposable endoscopic instruments, some surgeons may choose to reuse the disposable portion a few times before replacing it. In these situations, it is important to alert the surgeon and/or the surgical staff before the disposable portion has been used too many times. The counting mechanisms described in the other parent applications do not specifically disclose how they can be used with endoscopic instruments having separable disposable and reusable parts.

SUMMARY OF THE INVENTION

It is therefore an object of the invention to provide an automatic mechanism for tracking the number of times a surgical instrument has been used.

It is also an object of the invention to provide a counter mechanism which is integral with a surgical instrument so that the instrument itself will display the number of times it has been used or the number of times it may still be used with confidence.

It is another object of the invention to provide a use counter for surgical instruments which is activated by the sterilization process.

It is a further object of the invention to provide a mechanism by which a use counter for surgical instruments will not be erroneously triggered before an initial use of the surgical instrument.

It is yet another object of the invention to provide a use counter for endoscopic surgical instruments which will count up to a preset number and not repeat.

It is a further object of the invention to eliminate the need for a direction limiting pawl inside a rotating ratchet ring counter thereby simplifying construction of miniaturized counters.

Another object of the invention is to provide a use counter for endoscopic surgical instruments having separate mating handle and distal end portions.

Yet another object of the invention is to provide a pre-use locking mechanism for a use counter on a distal portion of an endoscopic surgical instrument having separate mating handle and distal portions, where prior to a first use of the distal portion, the locking mechanism prevents erroneous triggering of the counter, and upon a first use of the distal portion, the counter is automatically activated.

An additional object of the invention is to provide a use counter for surgical instruments, where upon a predetermined number of uses, the counter automatically impedes or prevents use of the surgical instrument.

The instant invention is premised upon the concept that the number of uses of a surgical instrument may be counted by counting the number of times the instrument has been sterilized. The sterilization of medical devices is usually accomplished by one of two standard methods: autoclaving at a temperature of typically 220°–250° F., or ETO (ethylene oxide gas sterilization) at a temperature of typically 140°–150° F.

In accord with the aforestated objects of the invention, the surgical instrument use counter of the invention comprises a display window in a portion of the surgical instrument, and heat responsive means for advancing a use indicator viewable through the display window each time the surgical instrument is sterilized (subjected to heat). Typically, the use indicator incrementally advances each time the surgical instrument is subjected to sterilization. Preferably the advancing of the use indicator occurs as the surgical instrument cools. The preferred heat responsive means mechanism is a coiled bimetallic pawl which expands and contracts with changes in temperature, thereby causing the free end of the pawl to follow a radially arced path. By arranging the use indicator as a ratchet wheel with a plurality of inner teeth and an outside display surface, the coiled bimetallic pawl can expand over a ratchet tooth as the instrument and bimetallic pawl are heated, and then catch behind the tooth and advance the ratchet as the instrument and bimetallic pawl cool. As the ratchet is advanced, the outside display surface of the ratchet moves past the window in the instrument and displays a new use indication or incremental number. To prevent backward movement of the ratchet wheel, a plurality of outer teeth are provided on the wheel and a stopping tooth is provided outside the wheel to engage the outer teeth.

Preferred aspects of the invention include: arranging the inner teeth of the ratchet so that once the counter has reached its maximum value, no further activation is possible; providing a locking pin to prevent operation of the counter during shipping in hot climates; attaching the locking pin to the packaging of the endoscopic tool so that the counter is automatically activated when the tool is removed from its packaging; providing the counter as part of the ferrule coupled to the outer tube portion of the separable distal end of a surgical instrument having a separable proximal handle and distal end; and providing the counter with a disabling mechanism which disables use of the instrument after a predetermined number of uses. The ferrule has an inwardly extending tooth which engages the outer teeth of the ratchet wheel to prevent backward movement. The bimetallic coil is attached to the ferrule hub and engages the inner teeth of the ratchet wheel. The ferrule is also provided with a stepped bore holding a spring biased locking pin and the ratchet wheel has a stepped width portion engaged by the locking pin to prevent premature activation during shipping and to disable the instrument after a predetermined number of uses.

Additional objects and advantages of the invention will become apparent to those skilled in the art upon reference to the detailed description taken in conjunction with the provided figures.

BRIEF DESCRIPTION OF THE DRAWINGS

FIG. 2b is a detailed perspective view of the engaging end of the bimetallic element shown in FIG. 2a;

DETAILED DESCRIPTION OF THE PREFERRED EMBODIMENTS

Figure 1:
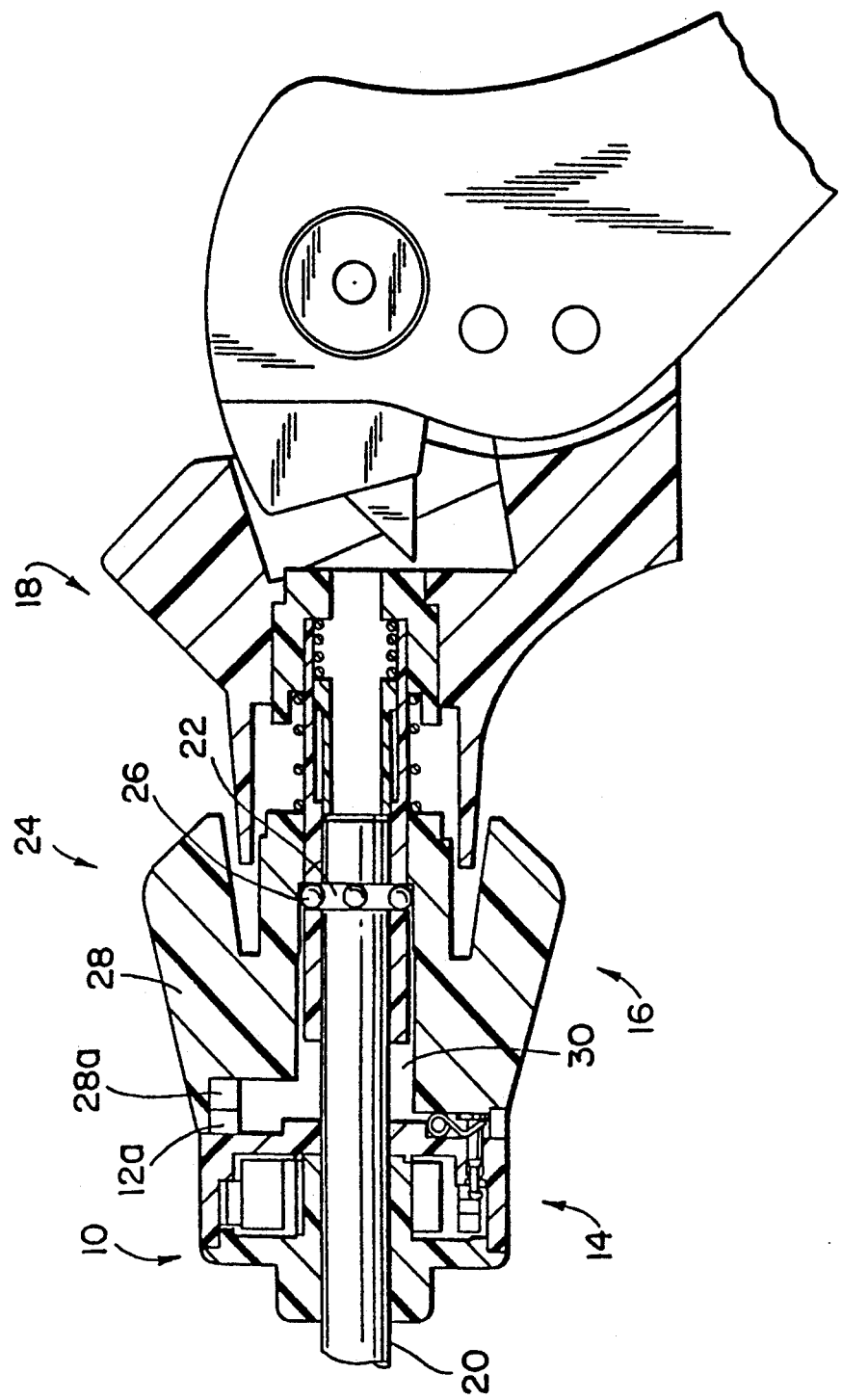
FIG. 1 is a longitudinal cross sectional view of a first embodiment of the invention mounted on the proximal coupling end of the distal separable portion of an endoscopic instrument having separable proximal handle and distal portions.

Turning now to FIG. 1, the improved sterilization counter 10 of the invention is shown mounted in the ferrule 12 of the distal portion 14 of an endoscopic instrument 16 having a separable proximal handle 18. As described in parent application Ser. No. 08/016,596, the distal portion 14 of the endoscopic instrument 16 includes a tube 20 upon which the ferrule 12 is mounted. The tube 20 is provided with a coupling means (a groove) 22 which engages a tube coupling means 24 in the handle portion 18. It will be noted that tube 20 also carries a push rod which is not shown herein since it is unimportant to the present invention. The tube coupling means 24 in the handle portion 18 generally includes a plurality of ball bearings 26 and a spring biased collar 28 having a stepped inner bore 30. Moving the collar 28 in the proximal direction (towards the handle 18) allows ball bearings 26 to enter the stepped inner bore 30 of the collar 28 and exit the groove 22 of the tube 20 thereby allowing an uncoupling of the two portions. The ferrule 12 is preferably provided with one or more engaging teeth 12a which engage corresponding teeth 28a on the sliding collar 28 of the handle portion 18 to prevent relative rotation of distal portion 14 and handle portion 18 after they are coupled.

Figure 2:
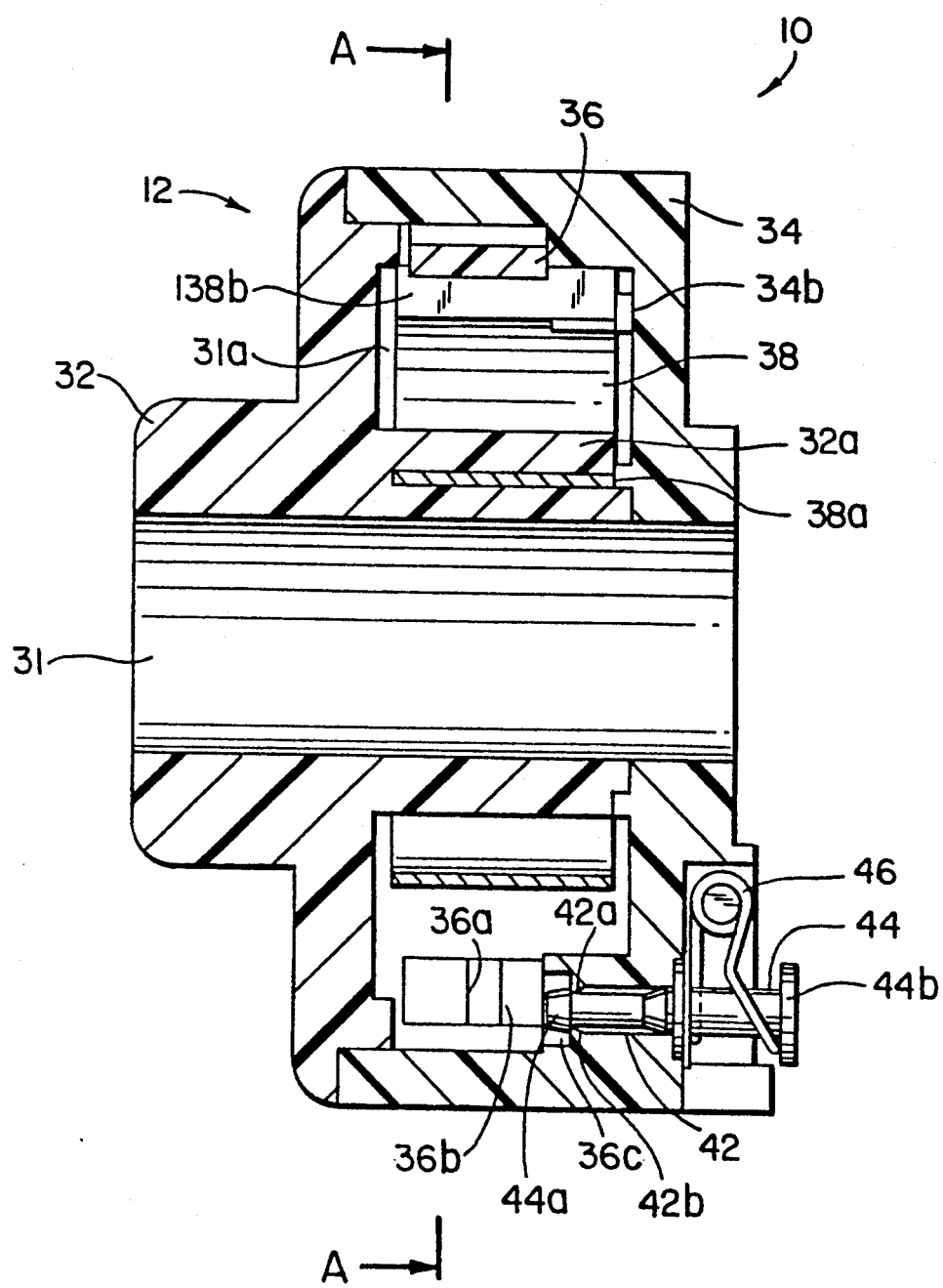
FIG. 2 is an enlarged cross sectional view of the first embodiment of the invention shown in FIG. 1.
Figure 2A:
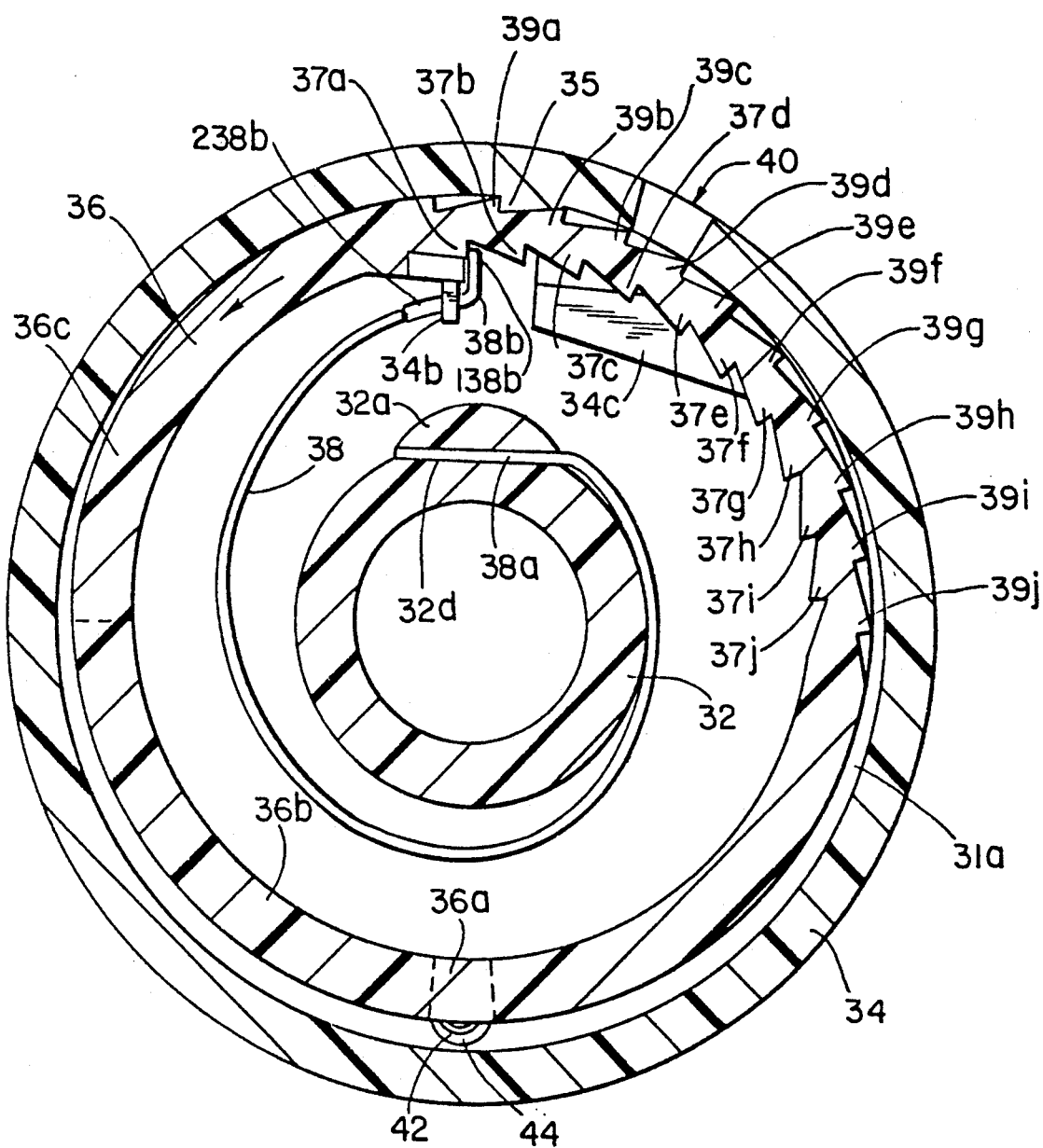
FIG. 2a is a cross section along the line A—A of FIG. 2.

FIGS. 2 and 2a show the counter 10 in greater detail. The counter 10 is contained in a housing (tube ferrule) 12 which includes an inner housing portion 32 and an outer housing portion 34. Both the inner housing 32 and the outer housing 34 are substantially annular, and when assembled, as shown in FIGS. 1 and 2, define an inner throughbore 31 through which tube 20 passes. In addition, when assembled, the inner housing 32 and the outer housing 34 define an annulus 31a in which the ratchet wheel 36 and a bimetallic element 38 are contained.

As shown in FIG. 2a, the ratchet wheel 36 is provided with ten inner ramped teeth 37a-37j and ten outer ramped teeth 39a-39j. The outer teeth 39a-39j are provided with sequential indicia (not shown) viewable through window 40 in outer housing 34. As explained in parent application Ser. No. 07/998,951, at least a portion of the ratchet wheel 36 is left without teeth so that upon advancing to a predetermined position it will advance no more. In accord with the invention, the ratchet wheel 36 has a stepped width portion 36a-36c (shown best in FIGS. 4a-4c) which is described in detail below. The ratchet wheel 36 has an outer diameter which is smaller than the inner diameter of outer housing portion 34 by an amount at least equal to the depth of its outer teeth.

Figure 2B:
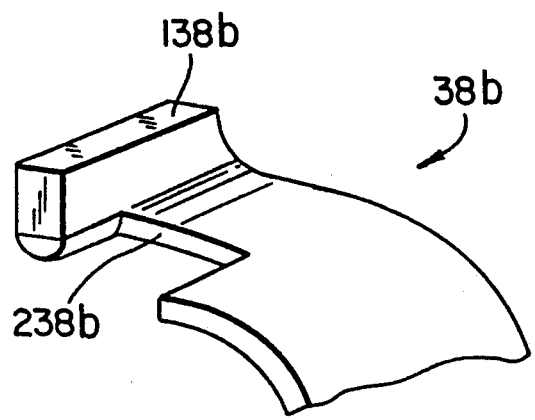

The bimetallic element 38 is a coil having a fixed end 38a and a free end 38b. It should be noted that the bimetallic coil is shown for clarity with only one turn, but that in actual practice, the coil may have several turns between fixed end 38a and free end 38b. The fixed end 38a is coupled to a hub portion 32a of the inner housing 32 by providing a chordal slit 32d in the hub and inserting the flat fixed end 38a into the slit. The free end 38b engages an inner tooth 37 of the ratchet wheel 36. As shown in FIGS. 2a and 2b, the free end 38b is preferably provided with an upturned engaging portion 138b and a notch 238b the function of which is described below.

The outer housing portion 34 is provided with an inwardly extending ramped tooth 35 and a stepped throughbore 42 carrying a locking pin 44 biased by a spring 46. The shoulder of the inwardly extending ramped tooth 35 engages the shoulder of one of the outer teeth 39a-39j of the ratchet wheel to prevent backward movement as described in detail below. The locking pin 44 engages the stepped width portion 36a-36c of the ratchet wheel to prevent counting during shipping and to disable the instrument 16 after a predetermined count has been reached as described in detail below.

The inner housing portion 32 is provided with a hub portion 32a for securing the fixed end 38a of bimetallic element 38 as mentioned above. In addition, the outer housing 34 or another portion of the housing other than the inner portion is provided with limiting stops 34b, 34c which limit movement of the free end 38b of bimetallic element 38 as described below.

Referring now to FIGS. 2, 2a, and 2b, the general operation of the counter 10 (disregarding for the moment the operation of the locking pin 44) is as follows. When the bimetallic element 38 is exposed to the temperature of sterilization, it expands so that the upturned portion 138b of its free end 38b pushes against inner tooth 37b urging it in the direction opposite the arrow shown in FIG. 2a. However, because the shoulder of the inwardly extending tooth 35 lockingly engages the shoulder of the outer tooth 39a, it prevents the ratchet wheel 36 from being moved in the direction opposite the arrow in FIG. 2a. Thus, the free end 38b of the bimettalic element 38 moves along tooth 37b (clockwise and radially inward as seen in FIG. 2a) until it engages tooth 37c and is stopped from further expanding movement by stop 34c. When the bimetallic element 38 cools after sterilization, the free end 38b contracts, pulling against tooth 37c in the direction of the arrow in FIG. 2a until tooth 37c is brought to the position occupied by tooth 37b in FIG. 2a. As the ratchet wheel 36 is advanced by the bimetallic element 38, the ramped surface of the outer tooth 39b is moved along the ramped surface of the inwardly extending tooth 35 until it is brought to the position occupied by tooth 39a in FIG. 2a. Further contracting movement of the free end 38b is prevented by a stop 34b which engages the notch 238b in the free end 38b. The advancement of the ratchet wheel as described above presents a next incremental indicia for viewing through a window 40 as described in the aforementioned parent applications.

As mentioned above, the ratchet wheel has an outer diameter which is somewhat smaller than the inner diameter of the outer housing 34. The bimetallic element 38 therefore biases the ratchet wheel up against the inwardly extending tooth 35 and the wheel 36 has room to move past the tooth 35 when the bimetallic element cools as described above.

Figure 2C:
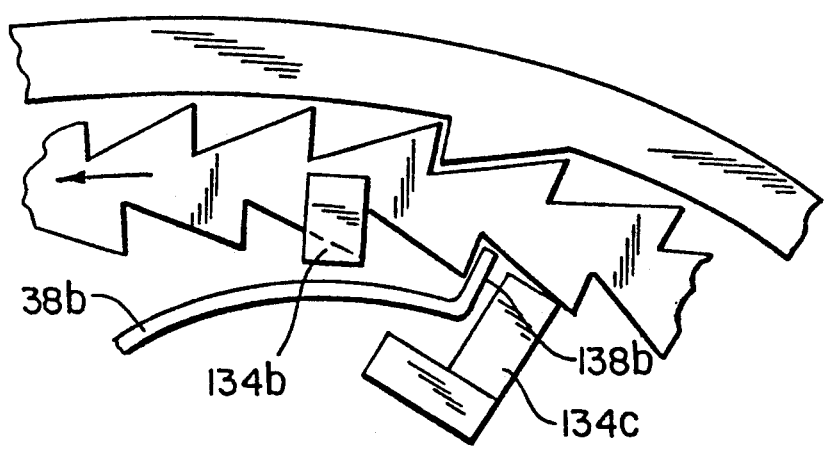
FIG. 2c is a partial view similar to FIG. 2a showing an alternate embodiment of the bimetallic element limiting stops.

It will also be appreciated that the upturned end 138b of the free end 38b of the bimetallic element 38 not only engages the inner teeth of the ratchet wheel but also coacts with the stop 34c to prevent movement over more than one tooth per temperature cycle. FIG. 2c shows a slightly different embodiment of stops 134b, 134c which limit movement of free end 38b without the need for a notch 238b. The block shaped stop 134b and L-shaped stop 134c prevent the bimetallic element 38 from advancing the ratchet wheel 36 more than one tooth at a time. The L-shaped stop 134c also keeps the free end of the bimetallic member from disengaging the ratchet wheel due to shock during sterilization.

Figure 3A:
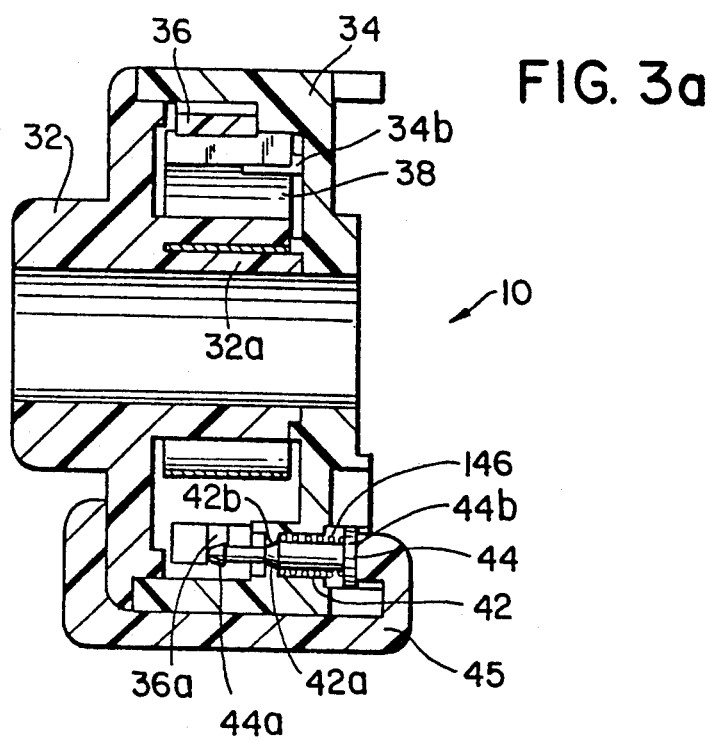
FIG. 3a is a view similar to FIG. 2, but of an alternate embodiment of biasing spring shown with the locking pin in the shipping position.
Figure 3B:
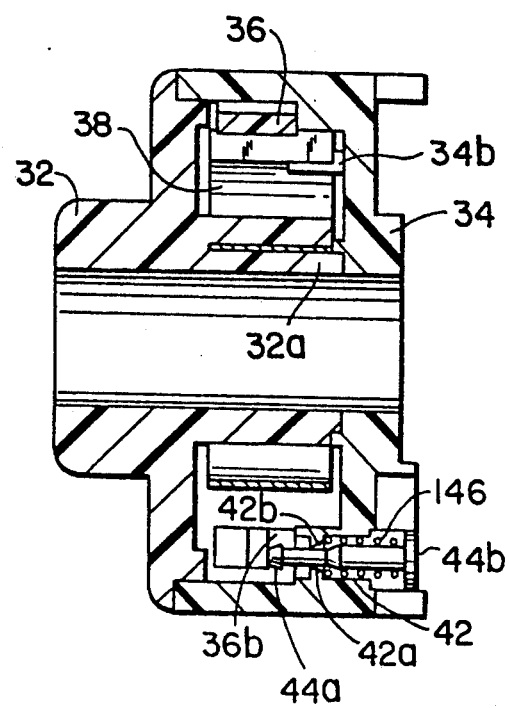
FIG. 3b is a view similar to FIG. 3a, but with the locking pin in the use position.
Figure 3C:
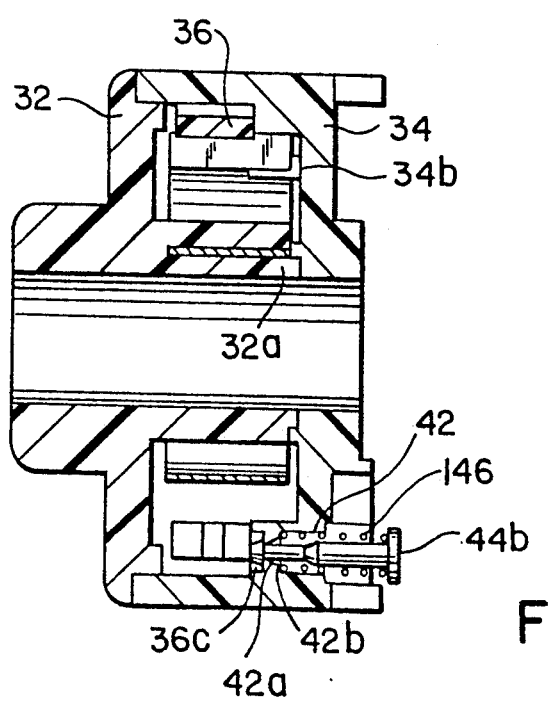
FIG. 3c is a view similar to FIG. 3a, but with the locking pin in the instrument disable position.

FIGS. 3a-3c and 4a-4c depict the locking pin arrangement of the invention in its three states. As mentioned above, the outer housing 34 of the counter 10 is provided with a stepped throughbore 42 near an outer edge of the housing. Through bore 42 is located to align with stepped width portion 36a-36c of the ratchet wheel 36 as seen best in FIG. 2a. Locking pin 44 is provided with a frustoconical nose 44a, a flat head 44b, and a shaft coupling the two. A spring 46 (FIG. 2) or 146 (FIGS. 3a-3c) is placed over the locking pin and the nose 44a of the pin is inserted through the narrow portion 42a of the stepped throughbore 42 where it snaps into place as shown in FIGS. 2 and 3c. A silicone seal 42b is preferably placed around the narrow portion 42a of the bore 42 to prevent foreign matter from entering the housing and jamming the counter.

Figure 4A:
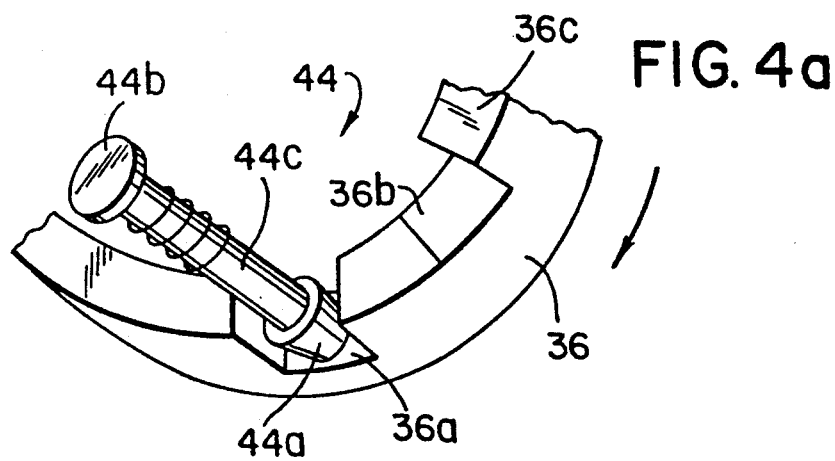
FIG. 4a is a perspective view of the locking pin in the shipping position.

FIGS. 3a and 4a show the locking pin 44 in the shipping position. It will be appreciated that during shipping, the distal portion 14 of instrument 16 (FIG. 1) is separated from handle 18 and contained in its own packaging (not shown). The ratchet wheel 36 is, at the time of shipping, in a first position (seen best in FIG. 4a) wherein its narrowest width 36a aligns with locking pin 44. Locking pin 44 is pressed in against ratchet wheel 36 into the recess formed by narrow width portion 36a so that rotation of the ratchet wheel is prevented. As mentioned above, the locking pin is biased away from the ratchet wheel by a spring (46 in FIG. 2, 146 in FIGS. 3a-3c) which can be a coil spring 146 or a hairpin spring 46 or any other type of spring. Thus, in order to keep the locking pin pressed against the ratchet wheel during shipping, a removable plastic clip 45 is applied across the flat head 44b of the locking pin 44 and around the housing 32 as shown in FIG. 3a. If desired, in lieu of clip 45, tape could be utilized. The tape could be attached to the packaging so that when the distal portion of the instrument is removed from the packaging for its first use, the tape is removed from the locking pin and the pin is disengaged from the ratchet wheel by the spring.

Figure 4B:
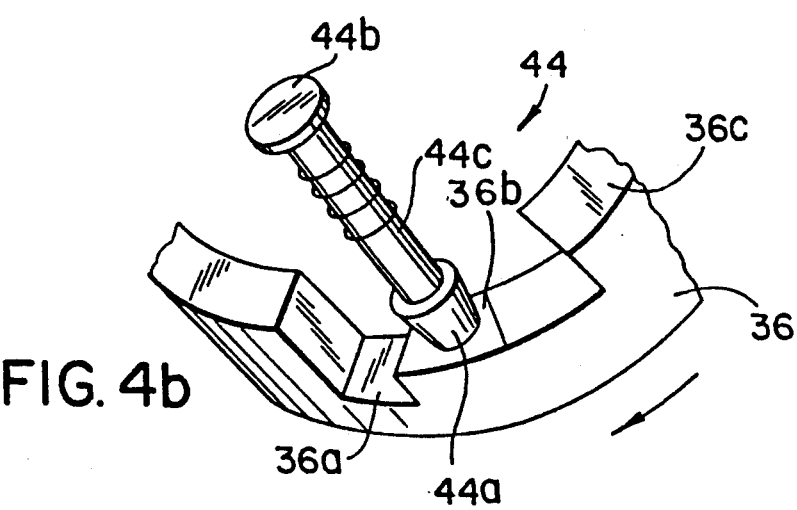
FIG. 4b is a view similar to FIG. 4a, but in the use position.

It will be appreciated that once the tape 45 is removed from the pin 44, the pin assumes the position shown in FIGS. 2 and 3c. However, the ratchet wheel is still in the position shown in FIG. 4a. When the distal portion 14 of the instrument 16 is coupled to the handle portion 18 as shown in FIG. 1, the locking pin 44 is pressed in towards the ratchet wheel to a position intermediate of the shipping position (FIG. 3a) and the fully extended position (FIGS. 2 and 3c). The dimensions of the pin and the ratchet wheel are chosen so that this intermediate position of the pin aligns its nose 44a with an intermediate width 36b of the ratchet wheel. As the counter 10 is subjected to the heating and cooling of sterilization, the ratchet wheel advances in the direction of the arrows shown in FIGS. 4a-4c. As the counter advances from its first count to its last count, the intermediate width 36b of the ratchet wheel 36 underlies the nose 44a of pin 44 as shown in FIG. 4b. Typically, the distal portion 14 of the instrument 16 will be removed from the handle portion 18 during sterilization. As mentioned above, when the two portions are uncoupled, the locking pin is moved to the position shown in FIG. 3c by action of the spring 146 (46 in FIG. 2). Recoupling the two portions moves the pin back to the intermediate position shown in FIGS. 3b and 4b. Comparing FIGS. 4b and 4c, it will be appreciated that once the counter has counted its last count, the wide portion 36c of the ratchet wheel 36 underlies the nose 44a of the locking pin 44 and that in this position, it is impossible for the pin 44 to be moved into the intermediate position (FIG. 3b). Therefore, the two portions of the surgical instrument cannot be recoupled once the ratchet wheel is advanced to the position shown in FIG. 4c since the locking pin is locked in the position shown in FIG. 3c and blocks the coupling of the two portions. This may be better understood with reference to FIG. 1, where it will be appreciated that if the head 44b of pin 44 extends rearward from the position shown, it will abut the ferrule 28 and force it in a proximal direction, thereby preventing the engagement of distal portion 14 of the endoscopic instrument 16 with the proximal handle 18 as described in the parent application Ser. No. 08/016,596.

Figure 4C:
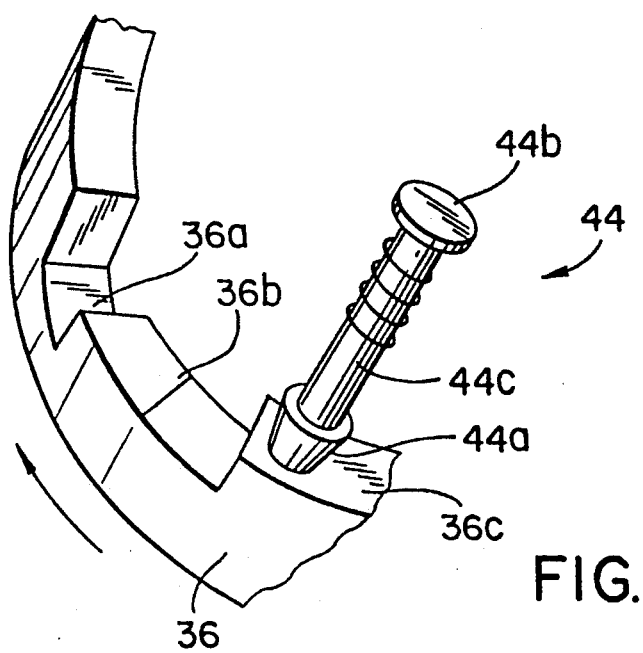
FIG. 4c is a view similar to FIGS. 4a and 4b, but in the instrument disable position.

It will be appreciated that in FIGS. 4a-4c, the angular length of intermediate width portion 36b of the ratchet wheel 36 is abbreviated for clarity. The actual length of the intermediate width portion 36b is more accurately depicted in FIG. 2a. Those skilled in the art will understand that the angular length of the intermediate width portion corresponds to the angular length of the indicia and teeth on the ratchet wheel.

There have been described and illustrated herein a use counter for an endoscopic instrument. While particular embodiments of the invention have been described, it is not intended that the invention be limited thereto, as it is intended that the invention be as broad in scope as the art will allow and that the specification be read likewise. Thus, while particular springs and stops have been disclosed, it will be appreciated that other mechanisms could be utilized to achieve substantially the same results in substantially the same manner. While the housing for the counter is disclosed as having an inner portion and an outer portion, those skilled in the art will realize that the housing may be configured in a number of different ways so long as there is a mounting place for the fixed end of the bimetallic element and a window to view the indicia on the ratchet ring. Moreover, the location of indicia and window are shown by example and could be relocated without departing from the spirit of the invention. Similarly, the number of teeth and the relative location of the stepped width portion of the ratchet wheel and the locking pin may be changed to suit particular applications. Additionally, while the invention has been disclosed for use with endoscopic instruments having separable proximal and distal portions, those skilled in the art will appreciate that features of the invention may be used in other types of endoscopic instruments. In particular, the arrangement of a ratchet wheel having inner and outer teeth where the outer teeth are engaged by an inward extending tooth may be applied in different types of counters to eliminate the need for a direction limiting pawl. It will therefore be appreciated by those skilled in the art that yet other modifications could be made to the provided invention without deviating from its spirit and scope as so claimed.

We claim:

1. An apparatus for counting the number of times a surgical instrument has been sterilized, said apparatus comprising:
    a) a housing having an inner hub portion and an outer cylindrical portion, said outer cylindrical portion having an inwardly extending tooth and an indication means;
    b) a ratchet wheel having a plurality of inner teeth, a plurality of outer teeth, and outer incremental indicia, said ratchet wheel being located between said inner hub portion and said outer cylindrical portion of said housing such that one of said plurality of outer teeth is engaged by said inward extending tooth and one of said incremental indicia is indicated by said indication means; and
    c) a bimetallic member having a free end and a fixed end, said free end engaging one of said plurality of inner teeth and said fixed end being attached to said inner hub portion of said housing, wherein
    a sterilization heating and cooling cycle causes said bimetallic member to engage a next one of said inner teeth and to advance said ratchet wheel past said inward extending tooth so that a next one of said incremental indicia is indicated by said indication means, and said inward extending tooth prevents said ratchet wheel from returning to a previous position.

2. An apparatus according to claim 1, wherein:
said inwardly extending tooth of said housing is a ramped tooth with a shoulder, and said plurality of inner teeth and plurality of outer teeth of said ratchet wheel are ramped teeth having shoulders.

3. An apparatus according to claim 1, wherein:
said bimetallic member is a coil.

4. An apparatus according to claim 1, wherein:
said plurality of inner teeth include a first tooth and a last tooth with a toothless space between said first and last tooth so that upon advancing said ratchet wheel to a last position it may not be advanced further.

5. An apparatus according to claim 1, further comprising:
    d) stop means adjacent said free end of said bimetallic member for limiting movement of said free end.

6. An apparatus according to claim 5, wherein:
said stop means includes a post extending from said housing, and said free end of said bimetallic member includes a notch within which said post extends.

7. An apparatus according to claim 1, further comprising:
    d) disengageable locking means engaging said ratchet wheel for preventing advancement of said ratchet wheel by said bimetallic coil member.

8. An apparatus according to claim 7, wherein:
said locking means comprises a spring biased pin and said ratchet wheel includes a notch engageable by said pin.

9. An apparatus according to claim 8, wherein:
said spring biased pin is held in a position engaging said notch by disengagable means attached to a package containing the surgical instrument so that when the surgical instrument is removed from the package, said disengagable means is removed from said spring biased pin and said pin is biased out of engagement with said notch.

10. An apparatus according to claim 1, wherein:
the surgical instrument has separable proximal and distal portions, the proximal portion of the surgical instrument having first coupling means for removably coupling with the distal portion of the surgical instrument and the distal portion of the instrument having second coupling means for removably coupling with the proximal portion of the instrument, and said apparatus further comprises,
    d) disabling means for preventing the proximal and distal portions of the surgical instrument from coupling after said ratchet wheel has been advanced to a predetermined position.

11. An apparatus according to claim 10, wherein:
said housing comprises a ferrule on the distal portion of said surgical instrument,
said disabling means includes a spring biased pin mounted in the ferrule and biased out of the ferrule,
said spring biased pin is pressed into said ferrule by said first coupling means when the proximal and distal portions of the surgical instrument are coupled, and
said ratchet wheel has a narrow width portion engageable by said pin when said pin is pressed into the ferrule and a wide width portion which prevents said pin from being pressed into the ferrule.

12. An apparatus according to claim 5, further comprising:
    e) disengageable locking means engaging said ratchet wheel for preventing advancement of said ratchet wheel by said bimetallic coil member.

13. An apparatus according to claim 12, wherein:
said locking means comprises a spring biased pin and said ratchet wheel includes a notch engageable by said pin, and
said spring biased pin is held in a position engaging said notch by disengagable means attached to a package containing the surgical instrument so that when the surgical instrument is removed from the package, said disengagable means is removed from said spring biased pin and said pin is biased out of engagement with said notch.

14. An apparatus according to claim 5, wherein:

the surgical instrument has separable proximal and distal portions, the proximal portion of the surgical instrument having first coupling means for removably coupling with the distal portion of the surgical instrument and the distal portion of the instrument having second coupling means for removably coupling with the proximal portion of the instrument, and said apparatus further comprises, e) disabling means for preventing the proximal and distal portions of the surgical instrument from coupling after said ratchet wheel has been advanced to a predetermined position.

15. An apparatus according to claim 14, wherein:

said housing comprises a ferrule on the distal portion of said surgical instrument, said disabling means includes a spring biased pin mounted in the ferrule and biased out of the ferrule, said spring biased pin is pressed into said ferrule by said first coupling means when the proximal and distal portions of the surgical instrument are coupled, and said ratchet wheel has a narrow width portion engageable by said pin when said pin is pressed into the ferrule and a wide width portion which prevents said pin from being pressed into the ferrule.

16. An apparatus according to claim 12, wherein:

the surgical instrument has separable proximal and distal portions, the proximal portion of the surgical instruments having first coupling means for removably coupling with the distal portion of the surgical instrument and the distal portion of the instrument having second coupling means for removably coupling with the proximal portion of the instrument, and said apparatus further comprises, f) disabling means for preventing the proximal and distal portions of the surgical instrument from coupling after said ratchet wheel has been advanced to a predetermined position.

17. An apparatus according to claim 16, wherein:

said housing comprises a ferrule on the distal portion of said surgical instrument, said disabling means includes a spring biased pin mounted in the ferrule and biased out of the ferrule, said spring biased pin is pressed into said ferrule by said first coupling means when the proximal and distal portions of the surgical instrument are coupled, and said ratchet wheel has a narrow width portion engageable by said pin when said pin is pressed into the ferrule and a wide width portion which prevents said pin from being pressed into the ferrule.

18. An apparatus according to claim 16, wherein:

said bimetallic member is a coil, and said plurality of inner teeth include a first tooth and a last tooth with a toothless space between said first and last tooth so that upon advancing said ratchet wheel to a last position it may not be advanced further.

19. An apparatus according to claim 18, wherein:

said inwardly extending tooth of said housing is a ramped tooth with a shoulder, and said plurality of inner teeth and plurality of outer teeth of said ratchet wheel are ramped teeth having shoulders.

* * * * *